(12) United States Patent
Hyde et al.

(10) Patent No.: US 8,718,817 B2
(45) Date of Patent: May 6, 2014

(54) PROGRAMMED DISPENSING OF CONSUMABLE COMPOSITIONS

(75) Inventors: Roderick A. Hyde, Redmond, WA (US);
Eric C. Leuthardt, St. Louis, MO (US);
Robert W. Lord, Seattle, WA (US);
Clarence T. Tegreene, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1695 days.

(21) Appl. No.: 12/001,061

(22) Filed: Dec. 7, 2007

(65) Prior Publication Data
US 2009/0149987 A1    Jun. 11, 2009

Related U.S. Application Data

(63) Continuation-in-part of application No. 11/998,461, filed on Nov. 29, 2007, and a continuation-in-part of application No. 12/001,063, filed on Dec. 7, 2007, now Pat. No. 7,804,419.

(51) Int. Cl.
*G06F 17/00* (2006.01)
*G08B 5/00* (2006.01)

(52) U.S. Cl.
USPC ........... 700/231; 700/237; 700/240; 700/242; 340/815.4

(58) Field of Classification Search
CPC .................................................. G07F 17/0092
USPC .................. 700/231–237, 240–242
See application file for complete search history.

(56) References Cited

U.S. PATENT DOCUMENTS

| | | | |
|---|---|---|---|
| 4,223,801 A | 9/1980 | Carlson | |
| 4,310,103 A | 1/1982 | Reilly, Jr. et al. | |
| 4,641,692 A | 2/1987 | Bennett | |
| 4,823,982 A | 4/1989 | Aten et al. | |
| 4,899,839 A | 2/1990 | Dessertine et al. | |
| 5,221,024 A | 6/1993 | Campbell | |
| RE34,337 E | 8/1993 | Bennett | |
| 5,329,459 A * | 7/1994 | Kaufman et al. | ............. 700/242 |
| 5,342,518 A | 8/1994 | Posner et al. | |
| 5,372,276 A | 12/1994 | Daneshvar | |
| 5,408,443 A | 4/1995 | Weinberger | |
| 5,454,406 A | 10/1995 | Rejret et al. | |
| 5,522,525 A | 6/1996 | McLaughlin et al. | |
| 5,651,887 A | 7/1997 | Posner et al. | |
| 5,681,507 A | 10/1997 | Kazuma | |
| 5,752,621 A | 5/1998 | Passamante | |
| 5,826,217 A | 10/1998 | Lerner | |

(Continued)

OTHER PUBLICATIONS

U.S. Appl. No. 12/927,038, Hyde et al.

*Primary Examiner* — Mohammad Z Shaikh
(74) *Attorney, Agent, or Firm* — Suiter Swantz pc llo

(57) ABSTRACT

Methods, systems and computer-readable mediums may provide for performing one or more operations including, but not limited to: obtaining dosing schedule data associated with a consumable composition regimen; dispensing of at least one dose of a consumable composition into a container according to the dosing schedule data associated with a consumable composition regimen; and detecting at least one indication of at least one ingestion of the consumable composition via from data from at least one sensor incorporated into the container configured to measure at least one property selected from: a physical property, a chemical property, an optical property or an electrical property.

15 Claims, 14 Drawing Sheets

(56) References Cited

U.S. PATENT DOCUMENTS

| | | | | |
|---|---|---|---|---|
| 5,850,344 | A * | 12/1998 | Conkright | 700/231 |
| 5,851,445 | A | 12/1998 | Kazuma | |
| 5,955,009 | A | 9/1999 | Kazuma | |
| 5,958,307 | A | 9/1999 | Kazuma | |
| 5,971,594 | A | 10/1999 | Sahai et al. | |
| 6,054,928 | A | 4/2000 | Lemelson et al. | |
| 6,068,156 | A | 5/2000 | Liff et al. | |
| 6,113,080 | A | 9/2000 | Kazuma | |
| 6,182,453 | B1 | 2/2001 | Forsberg | |
| 6,183,691 | B1 | 2/2001 | Swank et al. | |
| 6,249,717 | B1 | 6/2001 | Nicholson et al. | |
| 6,252,494 | B1 | 6/2001 | Howell | |
| 6,263,259 | B1 | 7/2001 | Bartur | |
| 6,304,797 | B1 | 10/2001 | Shusterman | |
| 6,330,957 | B1 | 12/2001 | Bell-Greenstreet | |
| 6,332,100 | B1 | 12/2001 | Sahai et al. | |
| 6,490,920 | B1 * | 12/2002 | Netzer | 73/304 C |
| 6,529,801 | B1 | 3/2003 | Rosenblum | |
| 6,539,281 | B2 | 3/2003 | Wan et al. | |
| 6,604,650 | B2 * | 8/2003 | Sagar | 221/3 |
| 6,625,518 | B2 | 9/2003 | Depeursinge | |
| 6,636,780 | B1 * | 10/2003 | Haitin et al. | 700/236 |
| 6,684,920 | B2 | 2/2004 | Seitz et al. | |
| 6,697,704 | B2 | 2/2004 | Rosenblum | |
| 6,732,884 | B2 | 5/2004 | Topliffe et al. | |
| 6,766,218 | B2 | 7/2004 | Rosenblum | |
| 6,773,668 | B1 | 8/2004 | Everson et al. | |
| 6,801,123 | B2 | 10/2004 | Brakus | |
| 6,856,932 | B1 | 2/2005 | Wallace | |
| 6,892,941 | B2 | 5/2005 | Rosenblum | |
| 7,072,738 | B2 | 7/2006 | Bonney et al. | |
| 7,175,081 | B2 | 2/2007 | Andreasson et al. | |
| 7,295,890 | B2 * | 11/2007 | Jean-Pierre | 700/244 |
| 7,440,818 | B2 | 10/2008 | Handfield et al. | |
| 7,444,203 | B2 | 10/2008 | Rosenblum | |
| 7,454,267 | B2 | 11/2008 | Bonney et al. | |
| 7,469,820 | B2 | 12/2008 | Rosenblum | |
| 7,471,993 | B2 | 12/2008 | Rosenblum | |
| 7,502,664 | B2 | 3/2009 | Berg | |
| 7,516,082 | B2 | 4/2009 | Sanville et al. | |
| 7,630,791 | B2 | 12/2009 | Nguyen et al. | |
| 7,715,277 | B2 * | 5/2010 | de la Huerga | 368/10 |
| 7,774,097 | B2 | 8/2010 | Rosenblum | |
| 7,804,419 | B2 | 9/2010 | Hyde et al. | |
| 7,831,336 | B2 | 11/2010 | Gumpert | |
| 7,844,361 | B2 * | 11/2010 | Jean-Pierre | 700/236 |
| 7,907,477 | B2 * | 3/2011 | Puzia | 368/10 |
| 8,019,471 | B2 | 9/2011 | Bogash et al. | |
| 8,060,249 | B2 | 11/2011 | Bear et al. | |
| 8,068,015 | B2 | 11/2011 | Burg | |
| 8,116,907 | B2 * | 2/2012 | Hyde et al. | 700/236 |
| 8,195,330 | B2 | 6/2012 | Coe | |
| 8,325,011 | B2 | 12/2012 | Butler et al. | |
| 8,362,914 | B2 * | 1/2013 | Hyde et al. | 340/815.4 |
| 8,457,783 | B2 * | 6/2013 | Hyde et al. | 700/240 |
| 2001/0011501 | A1 | 8/2001 | Sato et al. | |
| 2001/0045242 | A1 | 11/2001 | Clusserath et al. | |
| 2002/0001535 | A1 | 1/2002 | Weng | |
| 2002/0088817 | A1 | 7/2002 | Bell-Greenstreet | |
| 2003/0050731 | A1 | 3/2003 | Rosenblum | |
| 2003/0084957 | A1 | 5/2003 | Seitz et al. | |
| 2003/0088332 | A1 | 5/2003 | Rosenblum | |
| 2003/0093181 | A1 | 5/2003 | Rosenblum | |
| 2003/0220608 | A1 * | 11/2003 | Huitt et al. | 604/29 |
| 2004/0163970 | A1 * | 8/2004 | Sin et al. | 205/792 |
| 2004/0164146 | A1 | 8/2004 | Rosenblum | |
| 2004/0215369 | A1 | 10/2004 | Rosenblum | |
| 2004/0249250 | A1 | 12/2004 | McGee et al. | |
| 2005/0065645 | A1 | 3/2005 | Liff et al. | |
| 2006/0097000 | A1 | 5/2006 | Gumpert | |
| 2006/0259195 | A1 | 11/2006 | Eliuk et al. | |
| 2006/0266763 | A1 | 11/2006 | Svabo Bech | |
| 2006/0283876 | A1 | 12/2006 | Mocnik et al. | |
| 2007/0145067 | A1 | 6/2007 | Headlee | |
| 2007/0184219 | A1 | 8/2007 | Johnson | |
| 2007/0293982 | A1 | 12/2007 | Rosenblum | |
| 2008/0173705 | A1 | 7/2008 | Girard et al. | |
| 2008/0195251 | A1 | 8/2008 | Milner | |
| 2008/0283542 | A1 | 11/2008 | Lanka et al. | |
| 2009/0048712 | A1 | 2/2009 | Rosenblum | |
| 2009/0057341 | A1 | 3/2009 | Girard et al. | |
| 2009/0134181 | A1 | 5/2009 | Wachman et al. | |
| 2009/0144189 | A1 * | 6/2009 | Leuthhardt et al. | 705/38 |
| 2010/0324728 | A1 | 12/2010 | Rosenblum | |

* cited by examiner

PROGRAMMED DISPENSING OF CONSUMABLE COMPOSITIONS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application having United States Postal Service Express Mailing Label No. EM117518327US, entitled Programmed Dispensing of Consumable Compositions, naming Eric C. Leuthardt, Clarence T. Tegreene, Lowell L. Wood, Jr., Roderick A. Hyde and Robert W. Lord as inventors, filed Nov. 29, 2007, which is currently co-pending, or is an application of which a currently co-pending application is entitled to the benefit of the filing date.

For purposes of the USPTO extra-statutory requirements, the present application constitutes a continuation-in-part of U.S. patent application having United States Postal Service Express Mailing Label No. EM117519296, entitled Programmed Dispensing of Consumable Compositions, naming Roderick A. Hyde, Eric C. Leuthardt, Robert W. Lord, Clarence T. Tegreene and Lowell L. Wood, Jr. as inventors, filed Dec. 7, 2007, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http)://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Programmed regimens of consumable compositions may be prescribed by a physician or may simply be desirable for the health and well-being of an individual. However, confusion may arise concerning the schedule, dosage, and/or compliance with a programmed dosing regimen.

DETAILED DESCRIPTION

Figure 1:
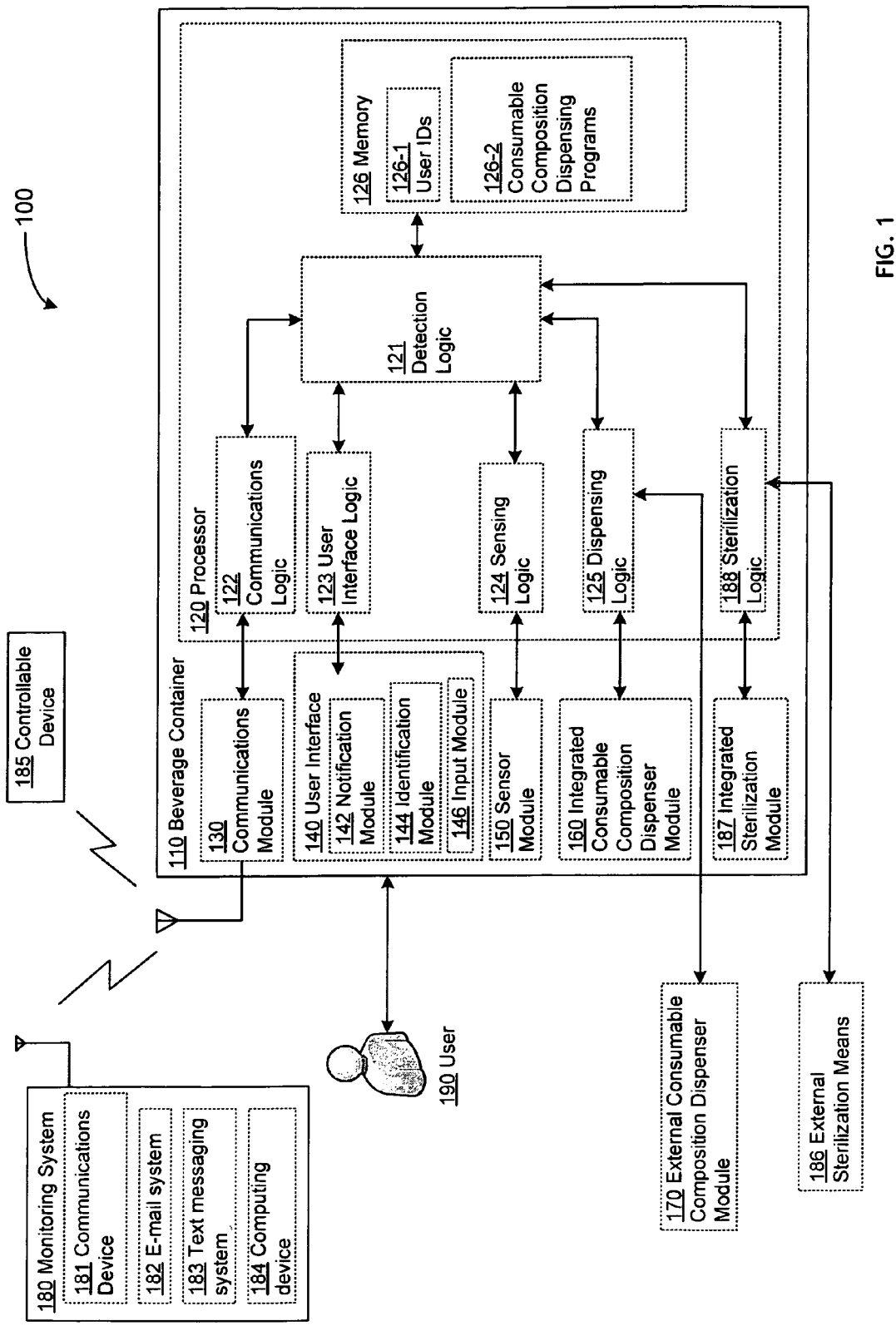
FIG. 1 shows a high-level block diagram of a beverage container.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example environment in which one or more technologies may be implemented. A consumable composition dispensing system 100 may comprise a beverage container 110 to be used by user 190. The beverage container 110 may include any receptacle configured for retaining a liquid or gel composition. For example, the beverage container 110 may include a cup, glass, mug, bowl, pitcher, jug, and the like.

The beverage container 110 may include a processor 120, a communications module 130, a user interface 140, a sensor module 150, an integrated consumable composition dispenser module 160, and/or an integrated sterilization module 187.

Processor 120 may include communications logic 122, user interface logic 123, sensing logic 124, dispensing logic 125, memory 126, and/or sterilization logic 188.

Memory 126 may include user identification data 126-1 and/or consumable composition dispensing programs 126-2.

User interface 140 may include a notification module 142, an identification module 144, and/or a user input module 146.

Sensor module 150 may include one or more of a light source sensor, a position sensor, an emission sensor, a spectrophotometer, an infrared or ultraviolet sensor, a biometric sensor and the like.

The consumable composition dispensing system 100 may further include an external consumable composition dispenser 170 and/or external sterilization module 186.

Figure 2:
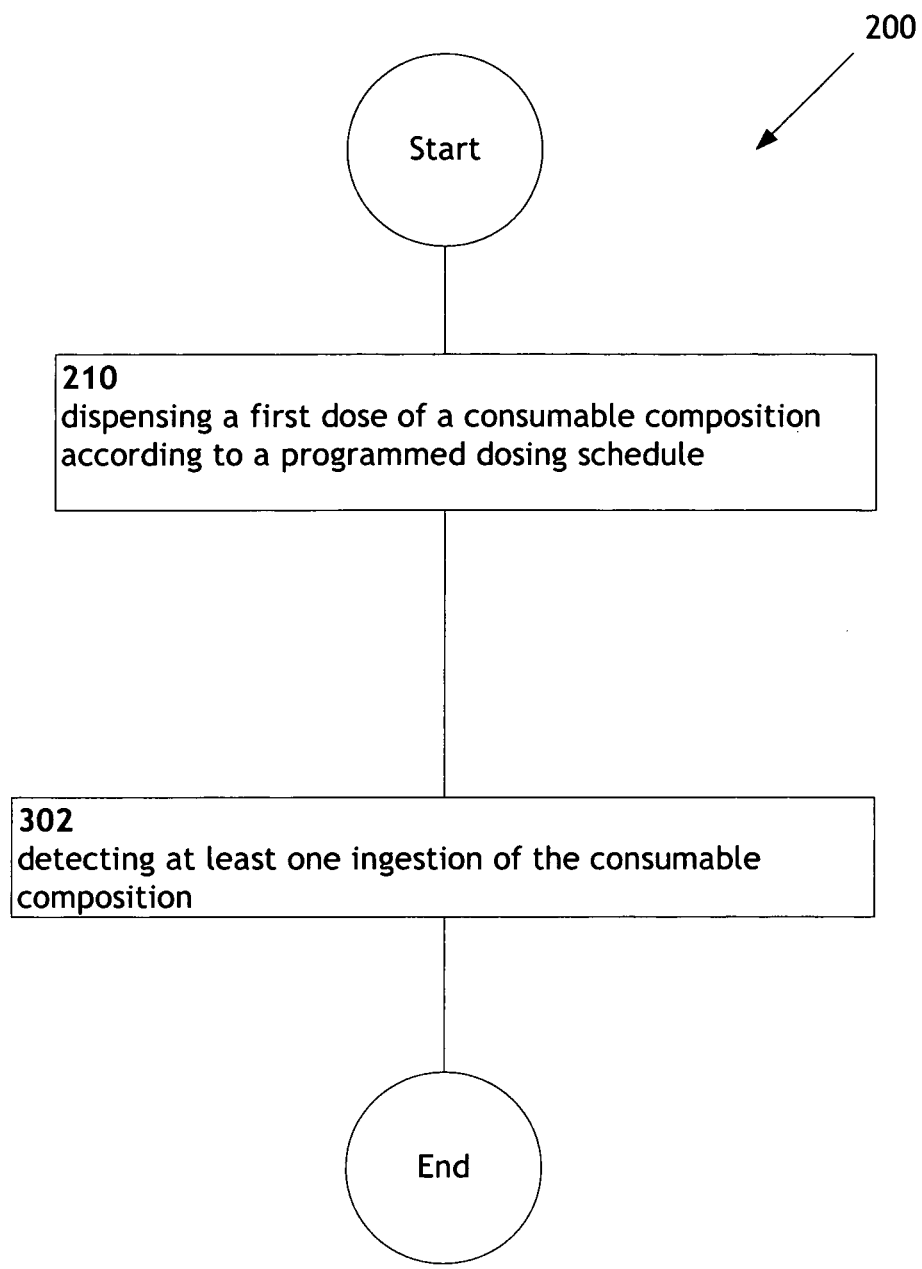
FIG. 2 is a high-level logic flowchart of a process.

FIG. 2 illustrates an operational flow 200 representing example operations related to programmed dispensing of consumable compositions. In FIG. 2 and in following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 200 moves to a dispensing operation 210, where dispensing a first dose of a consumable composition according to a programmed dosing schedule may occur (e.g. distributing a pharmaceutical composition in accordance with a user or physician-defined regimen). For example, as shown in FIG. 1, integrated consumable composition dispenser module 160, and or external consumable composition dispenser module 170 may distribute doses (e.g. 30 mg) of a consumable composition (e.g. an anti-depressant, such as Paroxotene) into a beverage container 110 (e.g. a cup).

The consumable composition may be a pharmaceutical composition including, but not limited to, one or more of the following: 5-alpha reductase inhibitors, 5-HT antagonists, ACE inhibitors, adrenergic agonists, adrenergic neurone blockers, alkalising agent, alpha blockers, aminoglycosides, anaesthetics, analgesics, androgens, angiotensin receptor blockers, anti-allergics, antiandrogens, antianginals, antiarrhythmics, antibiotics, anticholinergics, anticholinesterase, anticoagulants, anticonvulsants, antidepressants, antidiarrhoeals, antidopaminergics, anti-emetics, antiepileptics, antiflatulents, antifungal, antifungals, anti-hemophilics, antihistamine, antihistamines, antiplatelets, antipsychotics, antiseptics, antispasmodic, antispasmodics, antithyroid drugs, antitussives, anxiolytics, astringents, barbiturates, benzodiazepine, beta-receptor antagonists, beta-receptor blocker, bile acid sequestrants, bronchodilators, calcitonins, calcium channel blockers, cannabinoids, carbonic anhydrase inhibitors/hyperosmotics, cardiac glycosides, cerumenolyti, cholinergics, corticosteroids, COX-2 selective inhibitors, cycloplegics, cyclopyrrolone, cytoprotectants, decongestants, diphosphonates, diuretics, dopamine antagonist, emetic, fibrinolytics, fluoroquinolones, gonadotropins, growth hormones, H2-receptor antagonists, haemostatic drugs, heparins, hormonal contraceptives, hypnotics, hypolipidaemic agents, imidazoles, immunoglobulins, immunosuppressants, insulin, interferons, laxatives, local anesthetics, mast cell inhibitors, miotics, monoclonal antibodies, movement disorder drugs, mucolytics, muscle relaxants, mydriatics, neuromuscular drugs, nitrates, nitroglycerin, NSAIDs, ocular lubricants, opioids, parasympatholytics, parasympathomimetics, peripheral activators, polyenes, prostaglandin agonists/prostaglandin inhibitors, prostaglandin analogues, proton pump inhibitors, quinolones, reflux suppressants, selective alpha-1 blocker, sildenafil, statins, steroids, stimulants, sulfa drugs, sympathomimetics, thyroid hormones, topical anesthetics, topical antibiotics, vaccines, vasoconstrictors, vasodilators, vasopressin analogues, and the like.

The consumable composition may be a neutraceutical composition including, but not limited to, one or more of the following: vitamins (e.g., ascorbic acid, pyridoxine, riboflavin), minerals (e.g., calcium salts, zinc salts, potassium salts), hormones (e.g., cortisone, pancreatin, epinephrine), biochemicals (e.g., adenosine triphosphate, coenzyme A, cysteine), glandulars (e.g., thyroid, pancreas, adrenal cortex), herbals (e.g., ginkgo, garlic, goldenseal, echinacea), and the like.

At the operation 302, detecting at least one ingestion of the consumable composition may occur (e.g. a user has complied with a programmed dosing schedule for the consumable composition by swallowing the consumable composition). For example, as shown in FIG. 1, the sensing logic 124 may be operably coupled to sensor module 150. Upon ingestion of a consumable composition, the sensor module 150 may provide a signal to sensing logic 124 that ingestion has occurred.

Figure 3:
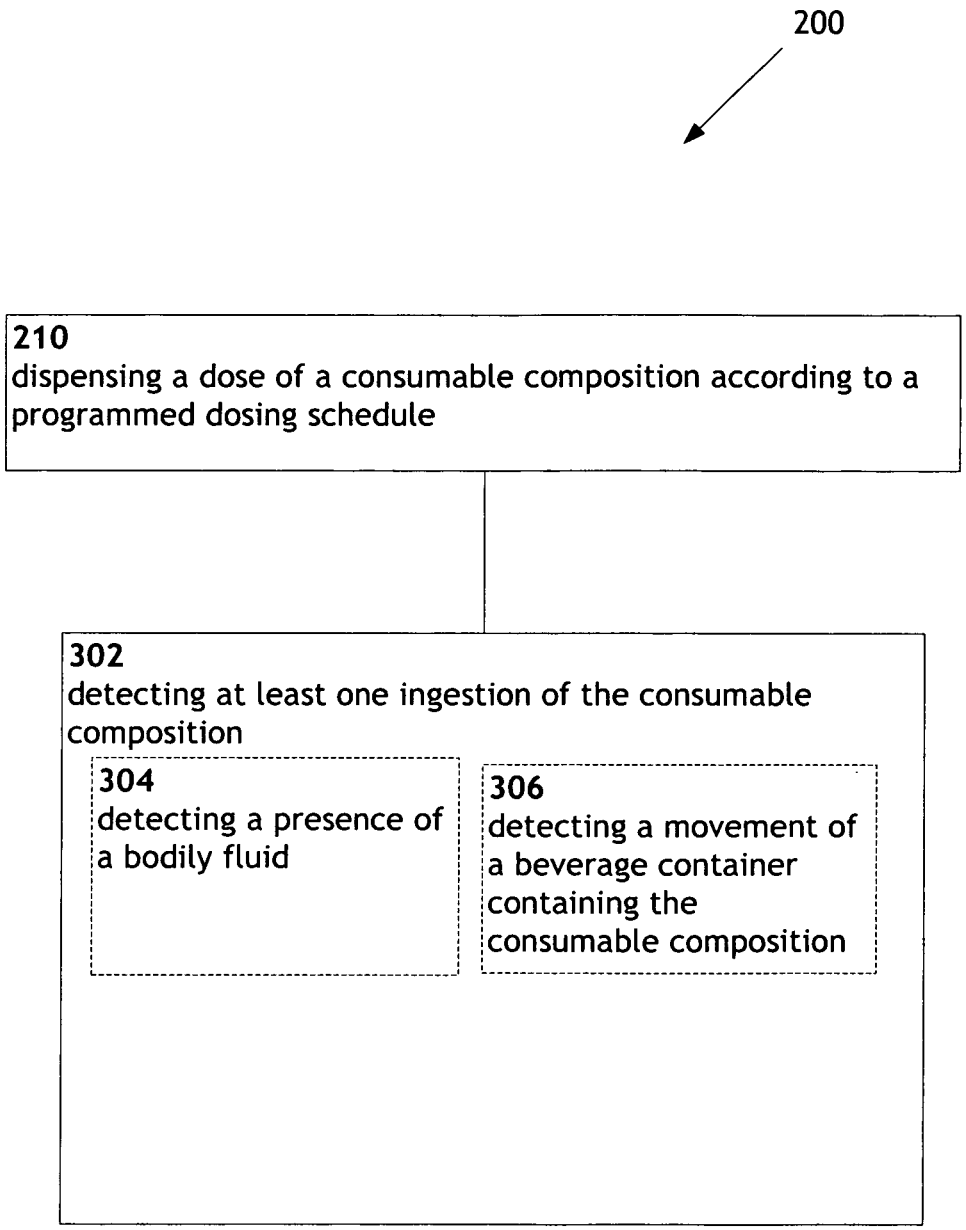
FIG. 3 is a high-level logic flowchart of a process depicting alternate implementations of FIG. 2.

FIG. 3 illustrates alternative embodiments of the example operational flow 200 of FIG. 2. FIG. 3 illustrates example embodiments where the detecting operation 302 may include at least one additional operation. Additional operations may include an operation 304, and/or an operation 306.

Further, at the operation 304, detecting a presence of a bodily fluid (e.g. biometric detection) may occur. For example, as shown in FIG. 1, the sensor module 150 may include a biometric sensor which senses the presence of saliva, perspiration, sebum and the like, either on the surface of the beverage container 110 or as a component of the contents therein.

At the operation 306, detecting a movement of a beverage container containing the consumable composition (e.g. accelerometric detection of a user-initiated movement) may occur. For example, as shown in FIG. 1, the sensor module 150 may include an accelerometer, inertial motion sensor and the like, which may sense the movement of the beverage container 110.

Figure 4:
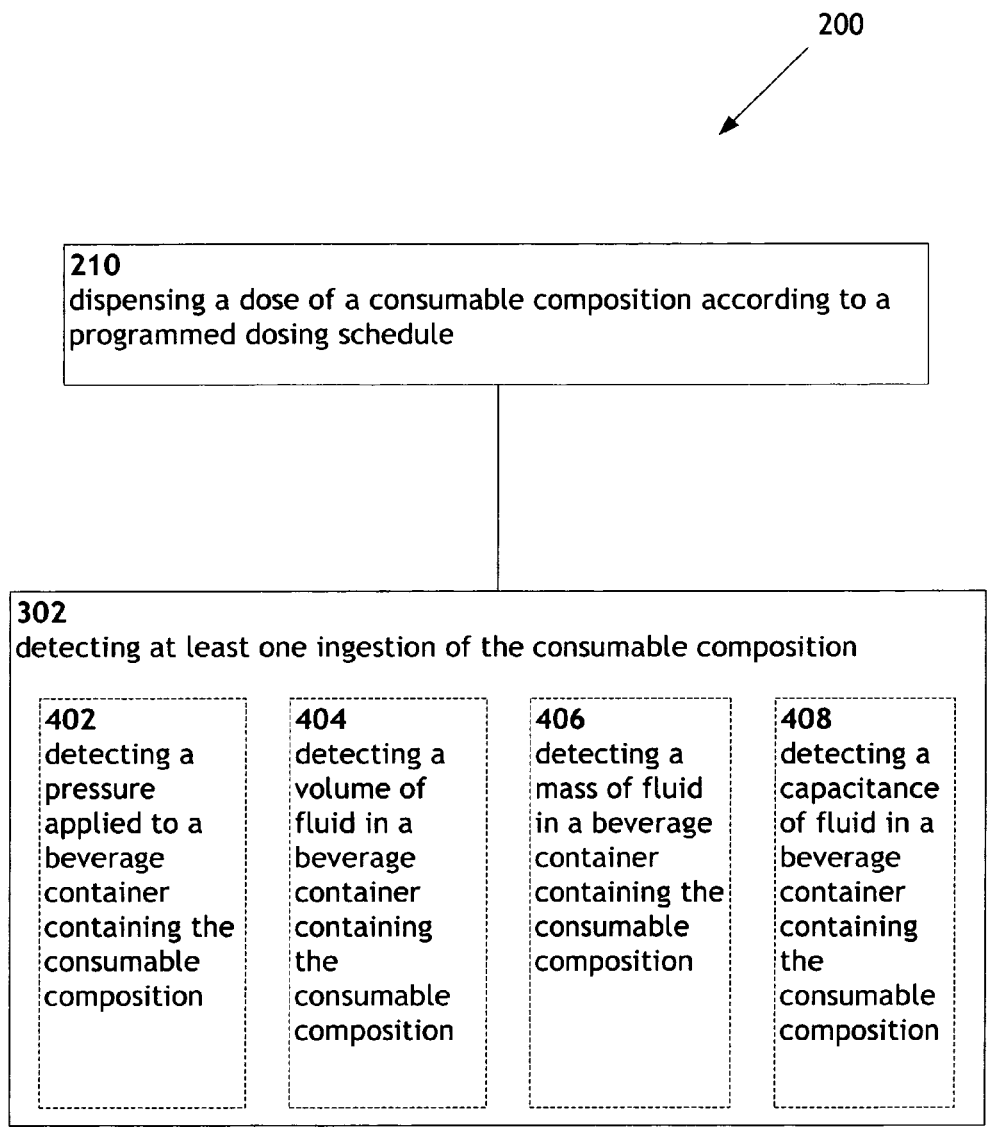
FIG. 4 is a high-level logic flowchart of a process depicting alternate implementations of FIG. 2.

FIG. 4 illustrates alternative embodiments of the example operational flow 200 of FIG. 2. FIG. 4 illustrates example embodiments where the detecting operation 302 may include at least one additional operation. Additional operations may include an operation 402, an operation 404, an operation 406, and/or an operation 408.

At the operation 402, detecting a pressure applied to a beverage container containing the consumable composition (e.g. fiber optic pressure detection of a user grasping the beverage container) may occur. For example, as shown in FIG. 1, the sensor module 150 may include a fiber optic pressure sensor, mechanical deflection pressure sensor, strain gauge pressure sensor, piezoresistive pressure sensor, microelectromechanical (MEMS) pressure sensor, variable capacitance pressure sensor, and the like which senses a pressure applied to the beverage container 110.

Similarly, at the operation 404, detecting a volume of fluid in a beverage container containing the consumable composition may occur (e.g. optical detection). For example, as shown in FIG. 1, the sensor module may include an optical or mechanical sensor which may sense a volume of the fluid in the beverage container 110.

At the operation 406, detecting a mass of fluid in a beverage container containing the consumable composition may occur (e.g. mechanical deflection pressure detection). For example, as shown in FIG. 1, the sensor module 150 may include a fiber optic pressure sensor, mechanical deflection pressure sensor, strain gauge pressure sensor, piezoresistive pressure sensor, microelectromechanical (MEMS) pressure sensor, variable capacitance pressure sensor, and the like which senses a mass of fluid contained in the beverage container 110.

At the operation 408, detecting a capacitance of fluid in a beverage container containing the consumable composition may occur (e.g. chemical field effect transistor detection). For example, as shown in FIG. 1, the sensor module 150 may include a capacitive concentration sensor which may sense a concentration of the consumable composition present in the beverage container 110.

Figure 5:
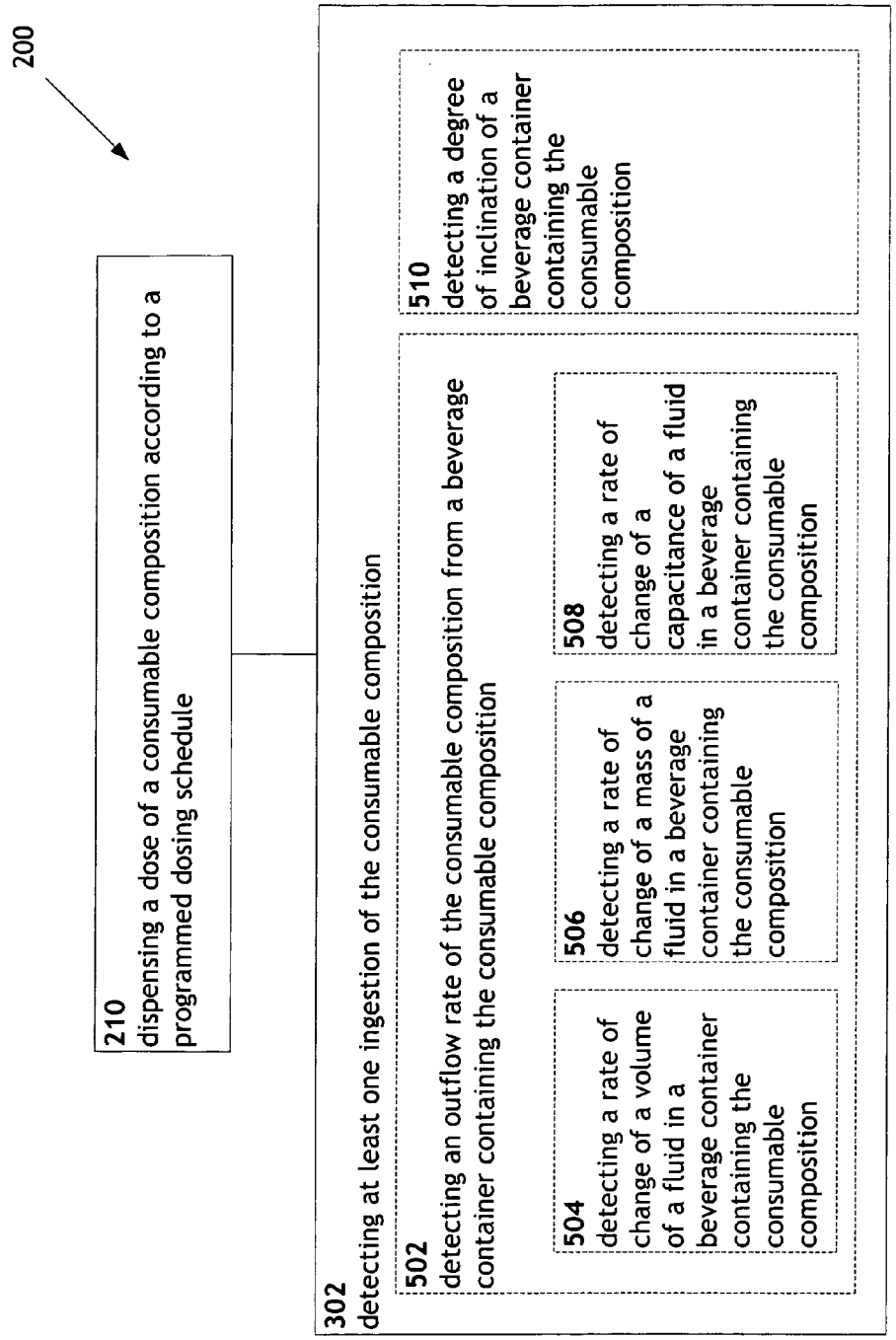
FIG. 5 is a high-level logic flowchart of a process depicting alternate implementations of FIG. 2.

FIG. 5 illustrates alternative embodiments of the example operational flow 200 of FIG. 2. FIG. 5 illustrates example embodiments where the detecting operation 302 may include at least one additional operation. Additional operations may include an operation 502, an operation 504, an operation 506, an operation 508, and/or an operation 510.

At the operation 502, detecting an outflow rate of the consumable composition from a beverage container containing the consumable composition may occur (e.g. a rate at which a physical, chemical, electrical, or optical property changes). For example, as shown in FIG. 1, the sensor module 150 may include a fiber optic pressure/outflow sensor, mechanical deflection pressure/outflow sensor, strain gauge pressure/outflow sensor, piezoresistive pressure/outflow sensor, microelectromechanical (MEMS) pressure/outflow sensor, variable capacitance pressure/outflow sensor, flowmeters, and the like which sense an outflow from the beverage container 110 containing the consumable composition. Such an outflow may indicate a proper ingestion or an improper disposal of the consumable composition, depending on the outflow rate. For example, proper ingestion might be indicated by an outflow rate indicative of normal drinking, while improper disposal might be indicated by an outflow rate indicative of dumping the contents of the cup by upending the cup.

Further, at the operation 504, detecting a rate of change of a volume of a fluid in a beverage container containing the consumable composition may occur (e.g. a magnetic flowmeter measuring volume outflow from the beverage container over time). Further, at the operation 506, detecting a rate of change of a mass of a fluid in a beverage container containing the consumable composition may occur (e.g. a piezoresistive pressure sensor measuring the change in the mass present in a beverage container over time). Further, at the operation 508, detecting a rate of change of a capacitance of a fluid in a beverage container containing the consumable composition may occur (e.g. a capacitive sensor measuring the change of capacitance of the fluid in the beverage container over time).

At the operation 510, detecting a degree of inclination of a beverage container containing the consumable composition may occur (e.g. a mechanism may detect that a user is rotating the beverage container by a certain degree relative to its designed resting position so as to ingest its contents). For example, as shown in FIG. 1, the sensor module 150 may include an inclinometer and the like. The degree of incline of the beverage container 110 may indicate a proper ingestion or an improper disposal of the consumable composition, depending on the degree of incline.

Figure 6:
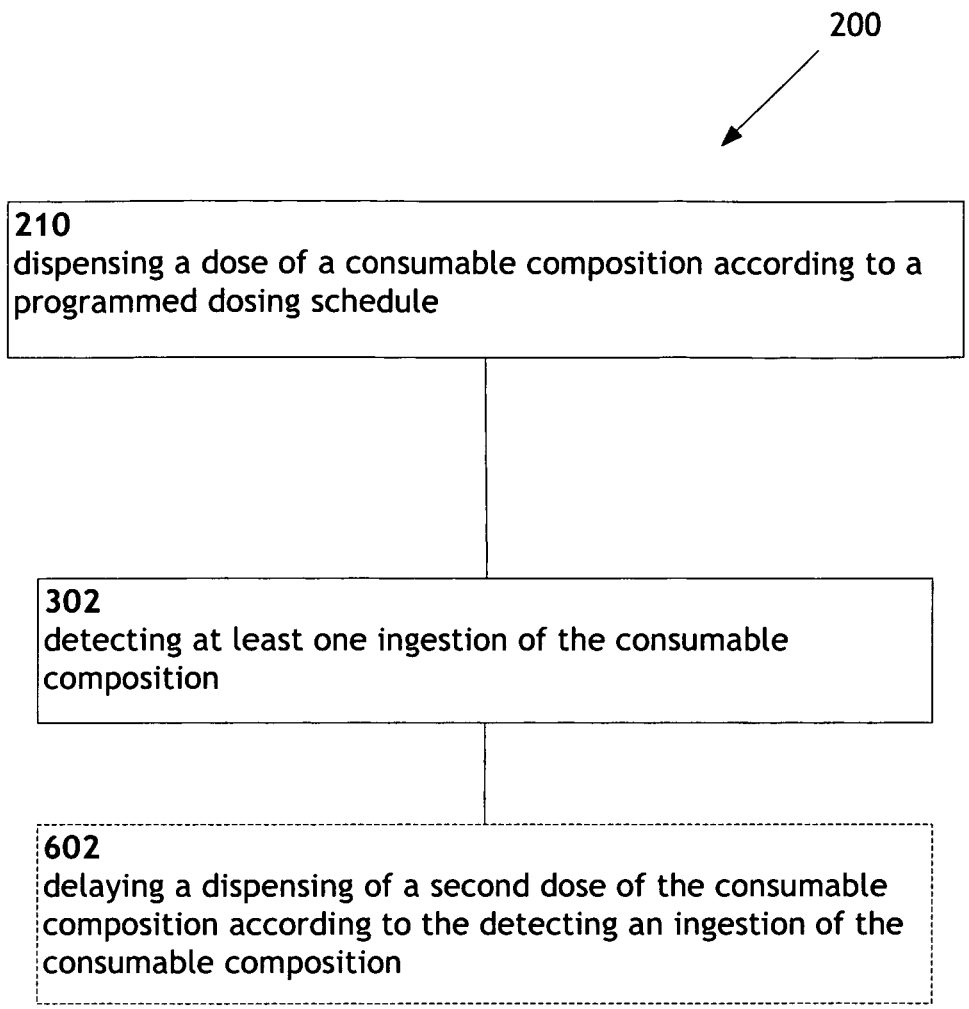
FIG. 6 is a high-level logic flowchart of a process depicting alternate implementations of FIG. 2.

FIG. 6 illustrates alternative embodiments of the example operational flow 200 of FIG. 2. FIG. 6 illustrates example embodiments where the operational flow 200 may include at least one additional operation. Additional operations may include a delaying operation 602.

At the operation 602, delaying a dispensing of a second dose of the consumable composition according to the detecting the at least one ingestion of the consumable composition may occur (e.g. a mechanism delaying dispensing until the first dose will have been metabolized). For example, as shown in FIG. 1, the sensing logic 124 may provide data from the sensor module 150 regarding an amount of consumable composition ingested to the detecting logic 121. The dispensing logic 125 may delay a dispensation of a second dose of the consumable composition by the integrated consumable composition dispenser module 160, and/or the external consumable composition dispenser module 170 until the detecting logic 121 indicates of an ingestion of a previously dispensed dose of the consumable composition.

Figure 7:
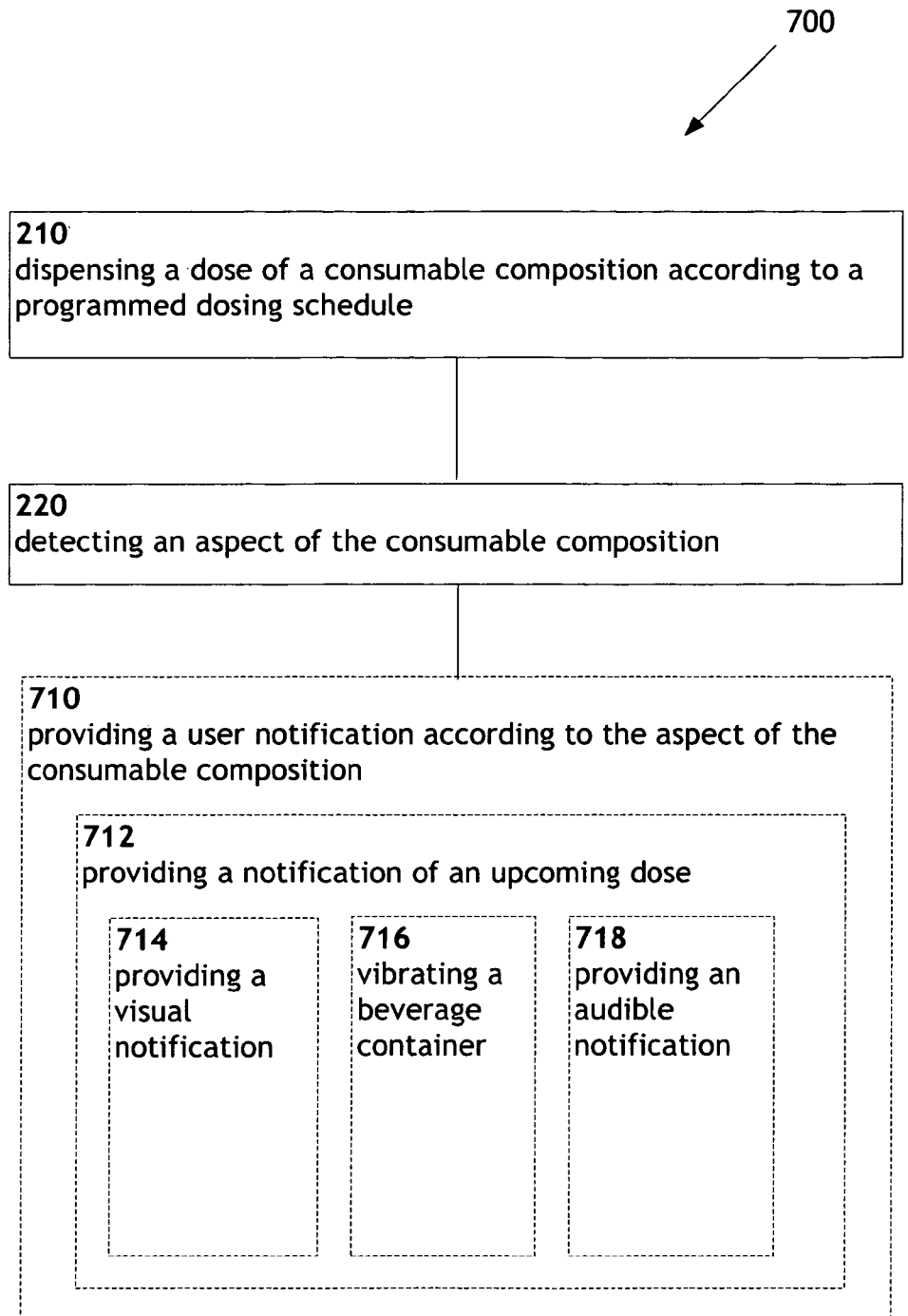
FIG. 7 is a high-level logic flowchart of a process.

FIG. 7 illustrates an operational flow 700 representing example operations related to dispensing a consumable composition. FIG. 7 illustrates an example embodiment.

At the detecting operation 220, detecting at least one aspect of the consumable composition (e.g. capacitive concentration detection) may occur. For example, as shown in FIG. 1, an aspect of the consumable composition may be detected by measuring a physical, chemical, optical, and/or electrical property with sensor module 150 operably coupled to sensing logic 124.

Further, an aspect of the consumable composition may be detected by receiving communications data from a communications module operably coupled to communications logic 122. An aspect of the consumable composition may be detected by accepting a user input by a user interface 140 operably coupled to user interface logic 123. An aspect of the consumable composition may be detected by receiving dispensing data from an integrated consumable composition dispenser module 160 and/or an external consumable composition dispenser module 170 operably coupled to dispensing logic 125. An aspect of the consumable composition may be detected by receiving sterilization data from an integrated sterilization module 186 and or an external sterilization module 187 operably coupled to sterilization logic 188.

The aspect of the consumable composition may include, but is not limited to, an amount of consumable composition dispensed into the beverage container 110, an amount of consumable composition present in the beverage container 110, an amount of the composition removed from the beverage container 110, an identity of the consumable composition, an identity of a user 190, a user input, a programmed schedule for dispensing the consumable composition, and the like.

The aspect of the consumable composition may be communicated via the communication module 130 to an outside entity. The outside entity may be a monitoring system 180 or a controllable device 185 which may be controlled according to the aspect of the consumable composition.

Monitoring system 180 may also transmit a notification (e.g. a notification that a programmed dosing schedule has been transmitted to the system 100) to a communications device 181 (e.g. a cell phone, satellite phone, Blackberry®, and/or land-line phone), e-mail system 182 (e.g. an IMAP, POP3, SMTP, and/or HTTP e-mail server having an e-mail account associated with a user 190), text messaging system 183 (e.g. SMS system in GSM) and/or a computing device 184 (e.g. a personal digital assistant (PDA), personal computer, laptop, music player and/or gaming device).

After a start operation, a dispensing operation 210, and a detecting operation 220, the operational flow 700 moves to a user notification operation 710, where providing a user notification according to the aspect of the consumable composition may occur (e.g. a notification of a dispensed dose of a consumable composition according to an amount of the consumable composition dispensed). For example, as shown in FIG. 1, the user interface logic 123 may cause the notification module 142 of the user interface 140 to provide a notification that an amount of consumable composition is about to be dispensed. The notification may include the identity of the consumable composition (e.g., a trade name and/or chemical composition of the consumable composition) and the timing of the dispensation (e.g. "20 minutes ago").

FIG. 7 further illustrates alternative embodiments of the example operational flow 700 of FIG. 7. FIG. 7 illustrates example embodiments where the notification operation 710 may include at least one additional operation. Additional operations may include an operation 712.

At the operation 712, providing a notification of an upcoming dose may occur (e.g. a dose scheduled according to a programmed dosing schedule will be dispensed at a given time). For example, as shown in FIG. 1, the user interface logic 140 may cause the notification module 142 of the user interface 140 to provide a notification to the user 190.

FIG. 7 further illustrates example embodiments where the upcoming dose notification operation 712 may include at least one additional operation. Additional operations may include an operation 714, an operation 716, and/or an operation 718.

At the operation 714, providing a visual notification may occur (e.g. a graphical notice on a display screen). For example, as shown in FIG. 1, the notification module 142 of the user interface 140 may include a flashing LED, LCD display screen, and the like.

At the operation 716, vibrating a beverage container may occur (e.g. movement of an asymmetrical mass). For example, as shown in FIG. 1, the notification module 142 may include an asymmetrical rotating mass operably coupled to a motor. Upon application of power to the motor, the mass may be rotated such that it induces vibration in the beverage container 110.

At the operation 718, providing an audible notification may occur (e.g. a simple beep or voice command). For example, as shown in FIG. 1, the notification module 142 of the user interface 140 may include a speaker assembly, and the like.

Figure 8:
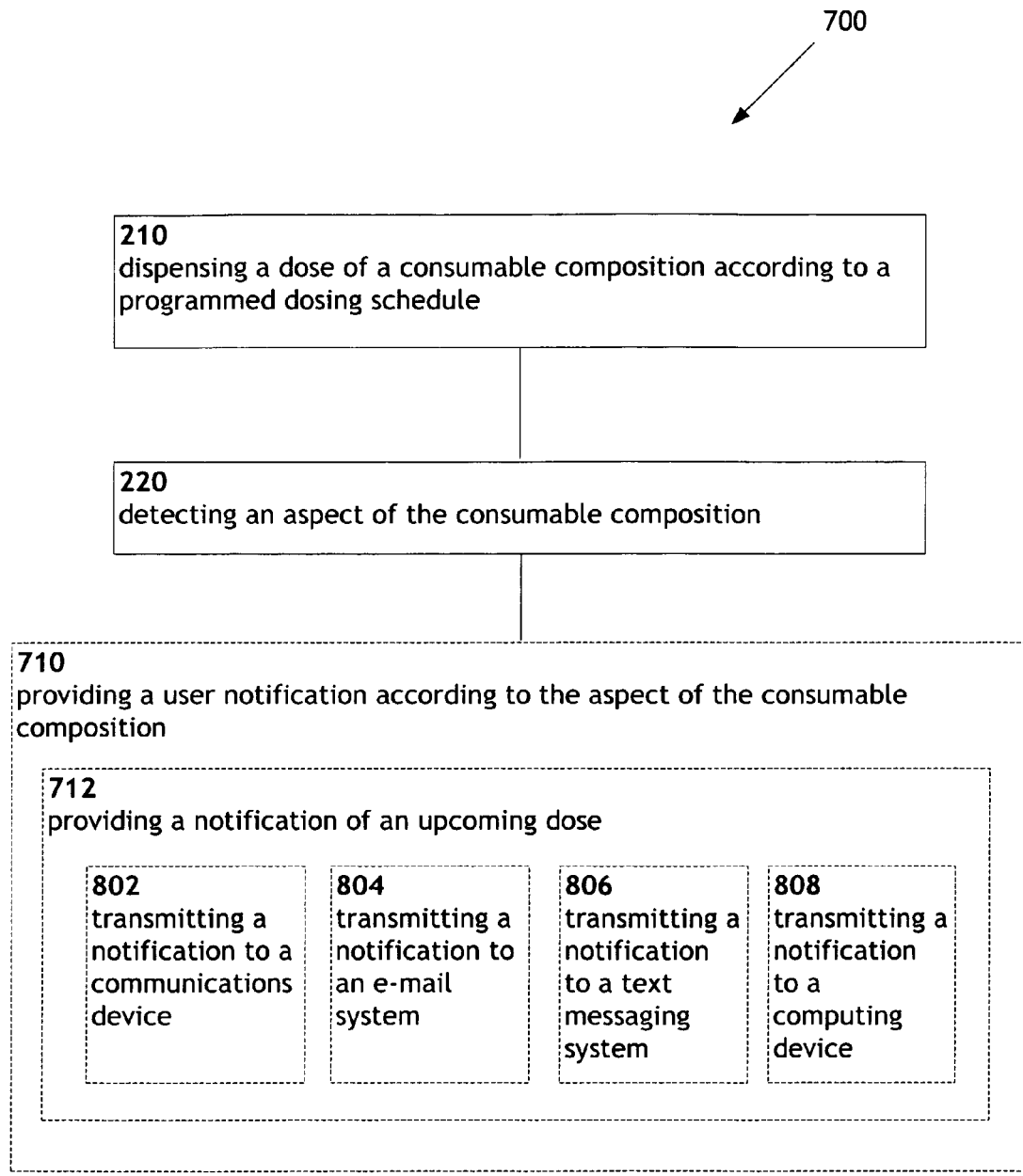
FIG. 8 is a high-level logic flowchart of a process depicting alternate implementations of FIG. 7.

FIG. 8 illustrates alternative embodiments of the example operational flow 700 of FIG. 7. FIG. 8 illustrates example embodiments where the upcoming dose notification operation 712 may include at least one additional operation. Additional operations may include an operation 802, an operation 804, an operation 806, and/or an operation 808.

At the operation 802, transmitting a notification to a communications device may occur (e.g. placing an automated call to a user's home phone). For example, as shown in FIG. 1, the communications module 130 may transmit a notification to a monitoring system 180 linked to a communications device 181. The communications device 181 may include a cell phone, satellite phone, Blackberry®, land-line phone, and the like.

At the operation 804, transmitting a notification to an e-mail system may occur (e.g. an automated e-mail notice to a user's e-mail account). For example, as shown in FIG. 1, the communications module 130 may transmit a notification to a monitoring system 180 linked to an e-mail system 182 including an IMAP, POP3, SMTP, and/or HTTP e-mail server having an e-mail account associated with a user 190.

At the operation 806, transmitting a notification to a text messaging system may occur (e.g. an automated text message to a user's cell phone). For example, as shown in FIG. 1, the communications module 130 may transmit a notification to a monitoring system 180 linked to a text messaging system 183, such as a SMS system in GSM.

At the operation 808, transmitting a notification to a computing device may occur (e.g. an automated instant message to a user's computer). For example, as shown in FIG. 1, the communications module 130 may transmit a notification to a monitoring system 180 linked to a computing device 184. The computing device 184 may include a personal digital assistant (PDA), personal computer, laptop, music player, gaming device, and the like capable of receiving instant messages from IM providers such as Microsoft®.

Figure 9:
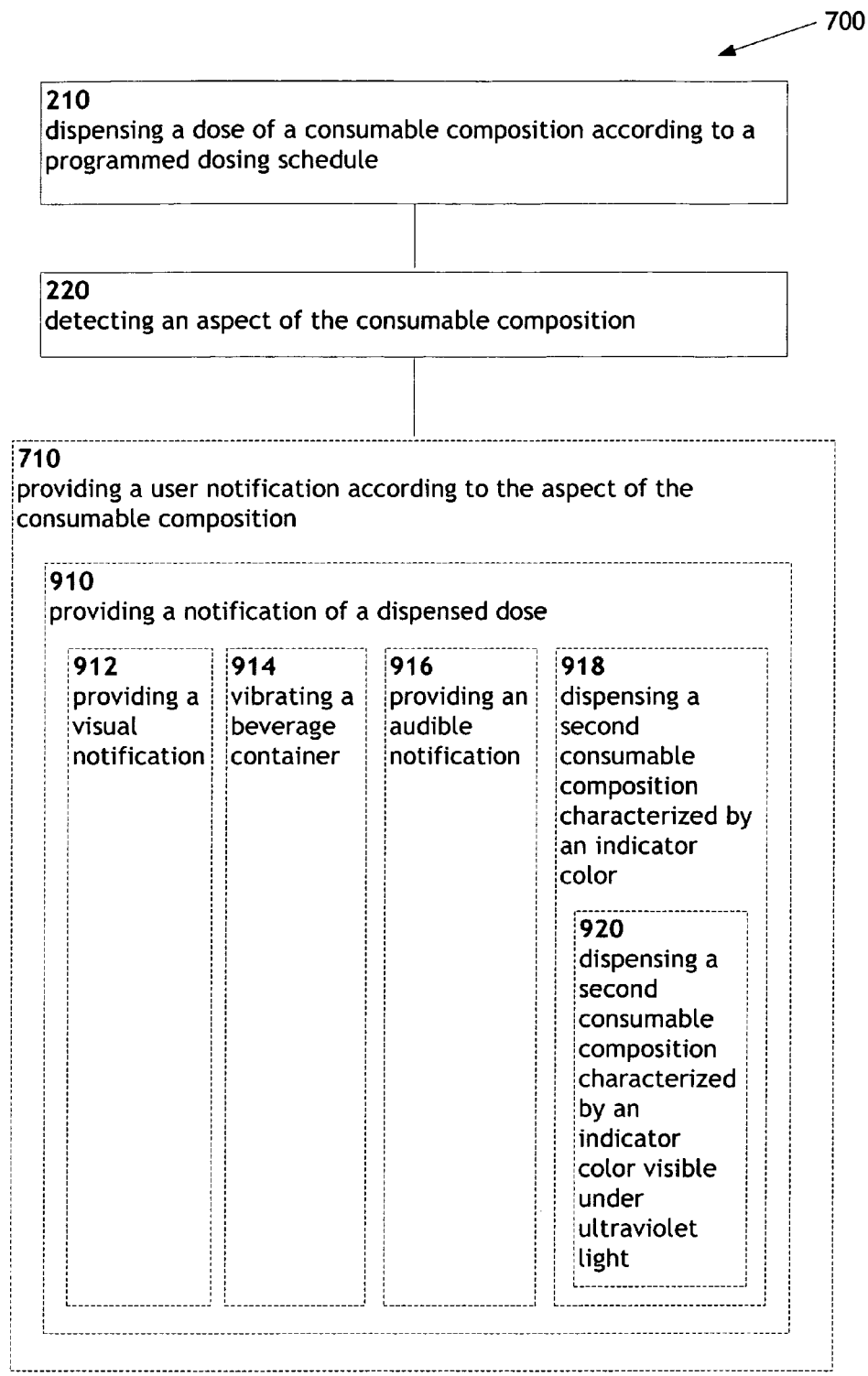
FIG. 9 is a high-level logic flowchart of a process depicting alternate implementations of FIG. 7.

FIG. 9 illustrates alternative embodiments of example operational flow 700 of FIG. 7. FIG. 9 illustrates an example embodiment where the user notification operation 710 may include at least one additional operation. Additional operations may include an operation 910.

At operation 910, providing a notification of a dispensed dose may occur (e.g. a dose scheduled according to a programmed dosing schedule has been dispensed at a given time). For example, as shown in FIG. 1, the user interface logic 123 may cause the notification module 142 of the user interface 140 to provide a notification that an amount of the consumable composition has been dispensed. The notification may include the identity of the consumable composition and the timing of the dispensation.

FIG. 9 further illustrates alternative embodiments of the example operational flow 700 of FIG. 7. FIG. 9 illustrates example embodiments where the dispensed dose notification operation 910 may include at least one additional operation. Additional operations may include an operation 912, an operation 914, an operation 916, an operation 918, and/or an operation 920.

At the operation 912, providing a visual notification may occur (e.g. an image of a beverage cup containing a consumable composition displayed on an LCoS display). For example, as shown in FIG. 1, the notification module 142 of the user interface 140 may include a flashing LED, an LCD or LCoS display screen, and the like.

At the operation 914, vibrating a beverage container may occur (e.g. periodic movement of an oscillating mass). For example, as shown in FIG. 1, the beverage container 110 may include an asymmetrical rotating mass operably coupled to a motor. Upon application of power to the motor, the mass may be rotated such that it induces vibration in the beverage container 110.

At the operation 916, providing an audible notification may occur (e.g. a vocal notification). For example, as shown in FIG. 1, the notification module 142 of the user interface 140 may include a speaker assembly, and the like, over which a notification may be transmitted. In some instances, the notification includes the dose dispensed and the material dispensed (e.g., "100 mg of Viagra was just dispensed into your cup").

At the operation 918, dispensing a second consumable composition characterized by an indicator color may occur (e.g. red, blue or green). For example, as shown in FIG. 1, the dispensing logic 125 may cause the integrated consumable composition dispenser module 160 and/or the external consumable composition dispenser module 170 to dispense a second consumable composition (e.g., Allura Red AC food coloring [2-naphthalenesulfonic acid]) which has a visible indicator color (e.g., red) different from the consumable composition (e.g., a white analgesic, such as acetylsalicylic acid). Further, at the operation 920, dispensing a second consumable composition characterized by an indicator color visible under ultraviolet light may occur (e.g. tonic water comprising quinine). Similarly, compositions visible under other electromagnetic radiation wavelength ranges, such as infrared, may be used.

Figure 10:
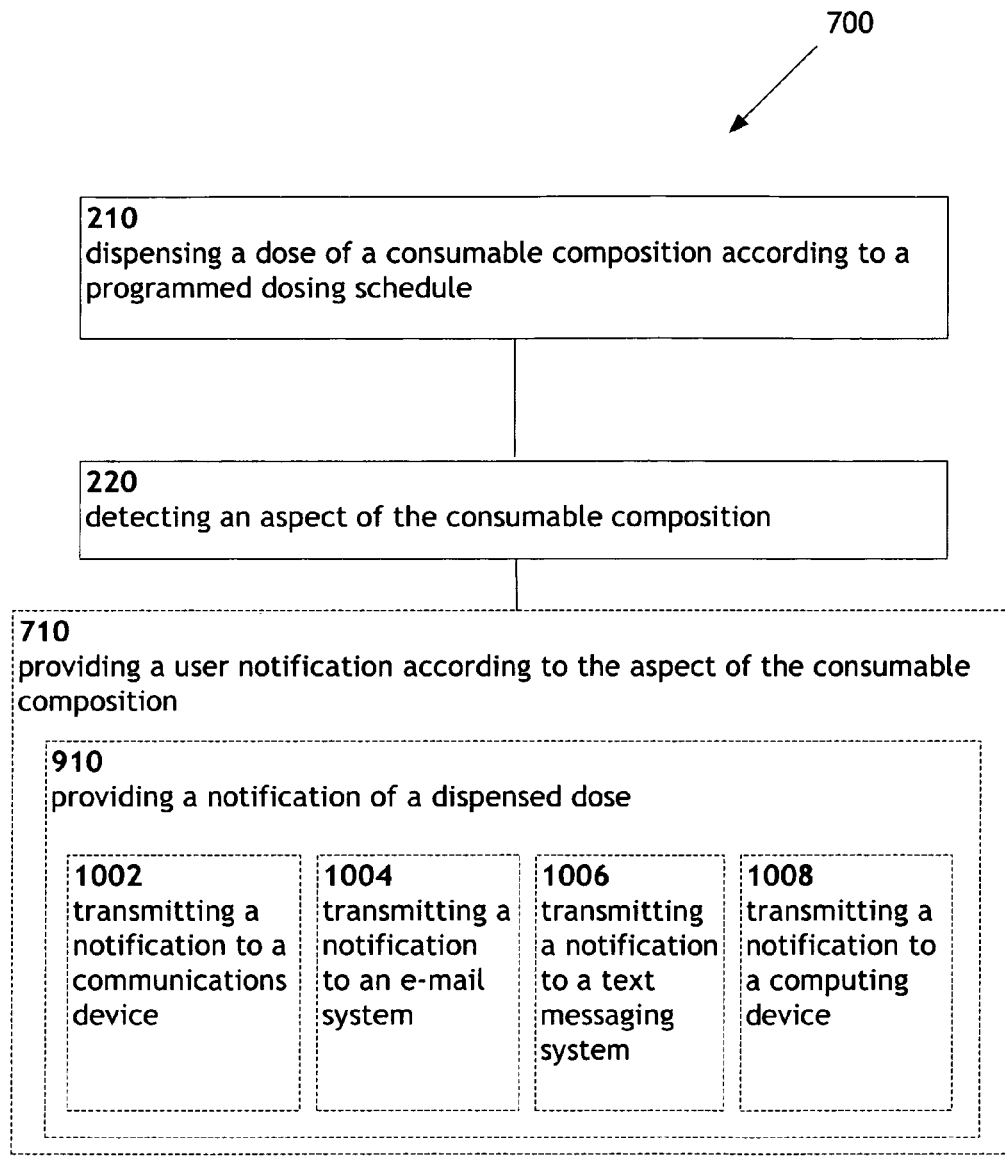
FIG. 10 is a high-level logic flowchart of a process depicting alternate implementations of FIG. 7.

FIG. 10 illustrates alternative embodiments of the example operational flow 700 of FIG. 9. FIG. 10 illustrates example embodiments where the dispensed dose notification operation 910 may include at least one additional operation. Additional operations may include an operation 1002, an operation 1004, an operation 1006, and/or an operation 1008.

At the operation 1002, transmitting a notification to a communications device may occur (e.g., sending a text message to a user's cell phone). For example, as shown in FIG. 1, the communications module 130 may transmit a notification to a monitoring system 180 linked to a communications device 181. The communications device 181 may include a cell phone, Blackberry®, land-line phone, and the like.

At the operation 1004, transmitting a notification to an e-mail system may occur (e.g. sending an e-mail to an IMAP, POP3, SMTP, and/or HTTP e-mail server having an e-mail account associated with a user 190). For example, as shown in FIG. 1, the communications module 130 may transmit a notification to a monitoring system 180 linked to an e-mail system 182.

At the operation 1006, transmitting a notification to a text messaging system may occur (e.g. sending text message to an SMS system in GSM). For example, as shown in FIG. 1, the communications module 130 may transmit a notification to a monitoring system 180 linked to a text messaging system 183.

At the operation 1008, transmitting a notification to a computing device may occur (e.g. sending an instant message to a personal computer). For example, as shown in FIG. 1, the communications module 130 may transmit a notification to a monitoring system 180 linked to a computing device 184. The computing device 184 may include a personal digital assistant (PDA), personal computer, laptop, music player, gaming device, and the like.

Figure 11:
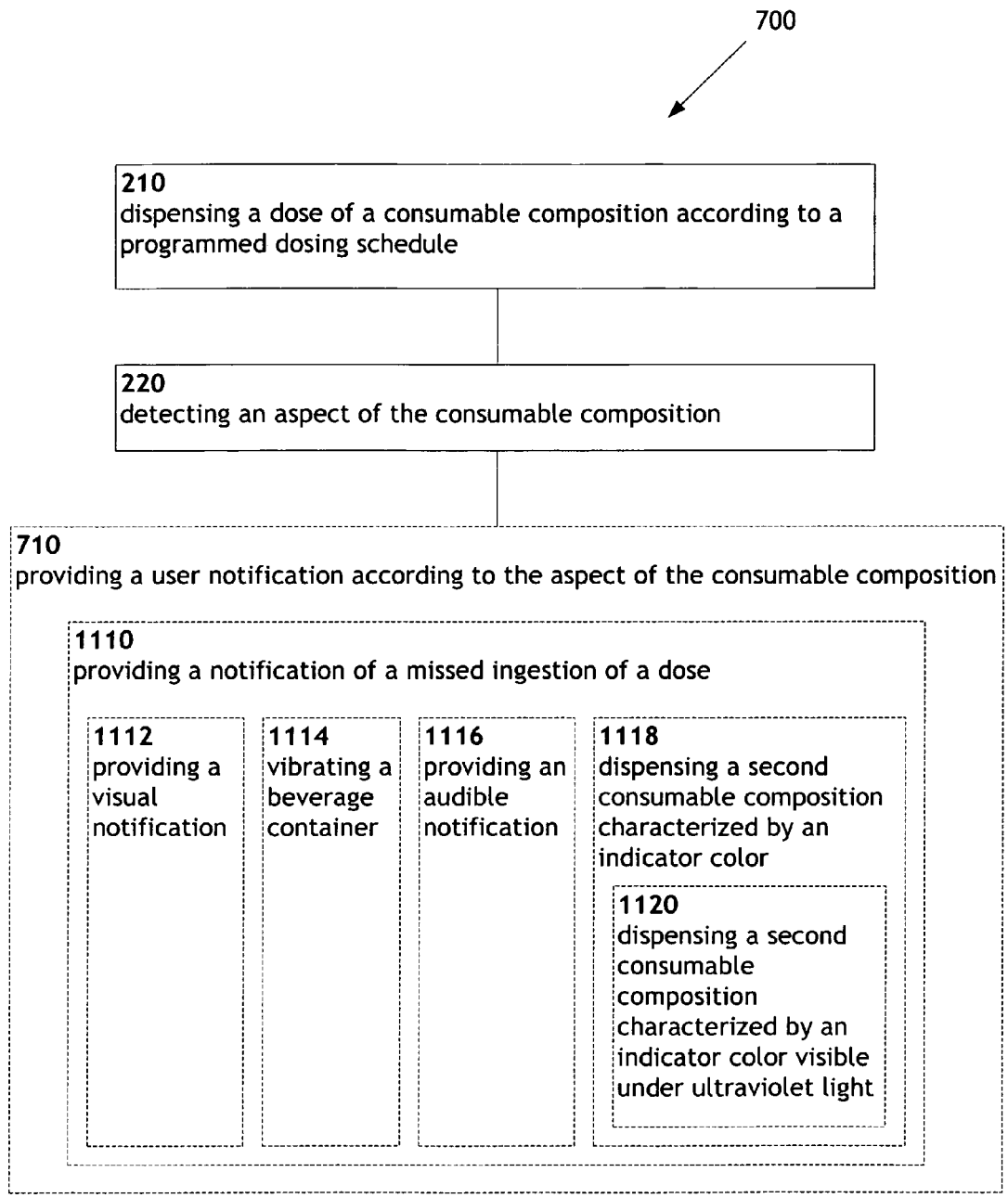
FIG. 11 is a high-level logic flowchart of a process depicting alternate implementations of FIG. 7.

FIG. 11 illustrates alternative embodiments of example operational flow 700 of FIG. 7. FIG. 11 illustrates an example embodiment where the user notification operation 710 may include at least one additional operation. Additional operations may include an operation 1110.

At operation 1110, providing a notification of a missed ingestion of a dose may occur (e.g. a dose dispensed according to a programmed dosing schedule has not been ingested). For example, as shown in FIG. 1, the user interface logic 123 may cause the notification module 142 of the user interface 140 to provide a notification that ingestion of the consumable composition has been missed. The notification may include the identity of the consumable composition and the timing of the dispensation (e.g., a dose of Percoset was dispensed at 3:00 pm).

FIG. 11 further illustrates alternative embodiments of the example operational flow 700 of FIG. 7. FIG. 11 illustrates example embodiments where the dispensed dose notification operation 1110 may include at least one additional operation. Additional operations may include an operation 1112, an operation 1114, an operation 1116, an operation 1118, and/or an operation 1120.

At the operation 1112, providing a visual notification may occur (e.g. an LED may change colors from green to red). For example, as shown in FIG. 1, the notification module 142 of the user interface 140 may include a flashing LED, LCD display screen, and the like.

At the operation 1114, vibrating a beverage container may occur (e.g. rotation of an asymmetrical mass). For example, as shown in FIG. 1, the beverage container 110 may include an asymmetrical rotating mass operably coupled to a motor. Upon application of power to the motor, the mass may be rotated such that it induces vibration in the beverage container 110.

At the operation 1116, providing an audible notification may occur (e.g. an audio broadcast of a ring tone). For example, as shown in FIG. 1, the notification module 142 of the user interface 140 may include a speaker assembly, and the like.

At the operation 1118, dispensing a second consumable composition characterized by an indicator color may occur. For example, as shown in FIG. 1, the dispensing logic 125 may cause the integrated consumable composition dispenser module 160 and/or the external consumable composition dispenser module 170 to dispense a second consumable composition (e.g., Sunset Yellow FCF food coloring [disodium salt of 6-hydroxy-5-[(4-sulfophenyl)azo]-2-naphthalenesulfonic acid]) separate from the consumable composition (e.g., an antihistamine) which has a visible indicator color (e.g. yellow) different color than the consumable composition (e.g. white). Further, at the operation 1120, dispensing a second consumable composition characterized by an indicator color visible under ultraviolet light may occur (e.g. a solution containing Vitamin B-12).

Figure 12:
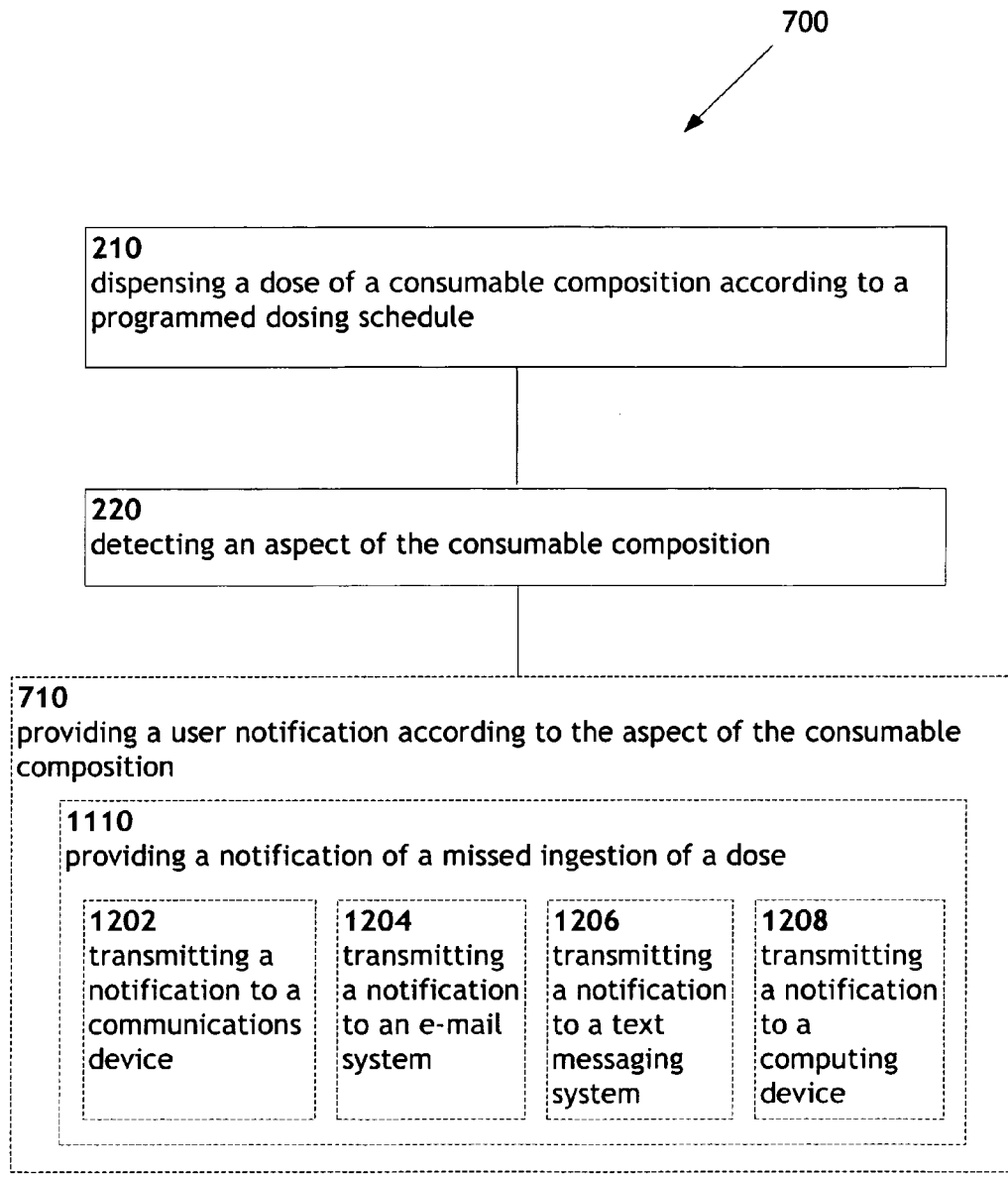
FIG. 12 is a high-level logic flowchart of a process depicting alternate implementations of FIG. 7.

FIG. 12 illustrates alternative embodiments of the example operational flow 700 of FIG. 11. FIG. 12 illustrates example embodiments where the missed dose ingestion notification operation 1110 may include at least one additional operation. Additional operations may include an operation 1202, an operation 1204, an operation 1206, and/or an operation 1208.

At the operation 1202, transmitting a notification to a communications device may occur (e.g. sending an instant message to a Blackberry® device). For example, as shown in FIG. 1, the communications module 130 may transmit a notification to a monitoring system 180 linked to a communications device 181. The communications device 181 may include a cell phone, Blackberry®, land-line phone, and the like.

At the operation 1204, transmitting a notification to an e-mail system may occur (e.g. an e-mail to an IMAP, POP3, SMTP, and/or HTTP e-mail server having an e-mail account associated with a user 190). For example, as shown in FIG. 1, the communications module 130 may transmit a notification to a monitoring system 180 linked to an e-mail system 182.

At the operation 1206, transmitting a notification to a text messaging system may occur (e.g. text message to an SMS system in GSM). For example, as shown in FIG. 1, the communications module 130 may transmit a notification to a monitoring system 180 linked to a text messaging system 183.

At the operation 1208, transmitting a notification to a computing device may occur (e.g., an instant message via an online gaming system, such as the Xbox Live® system marketed by the Microsoft® Corporation). For example, as shown in FIG. 1, the communications module 130 may transmit a notification to a monitoring system 180 linked to a computing device 184. The computing device 184 may include a personal digital assistant (PDA), personal computer, laptop, music player, gaming device, and the like.

Figure 13:
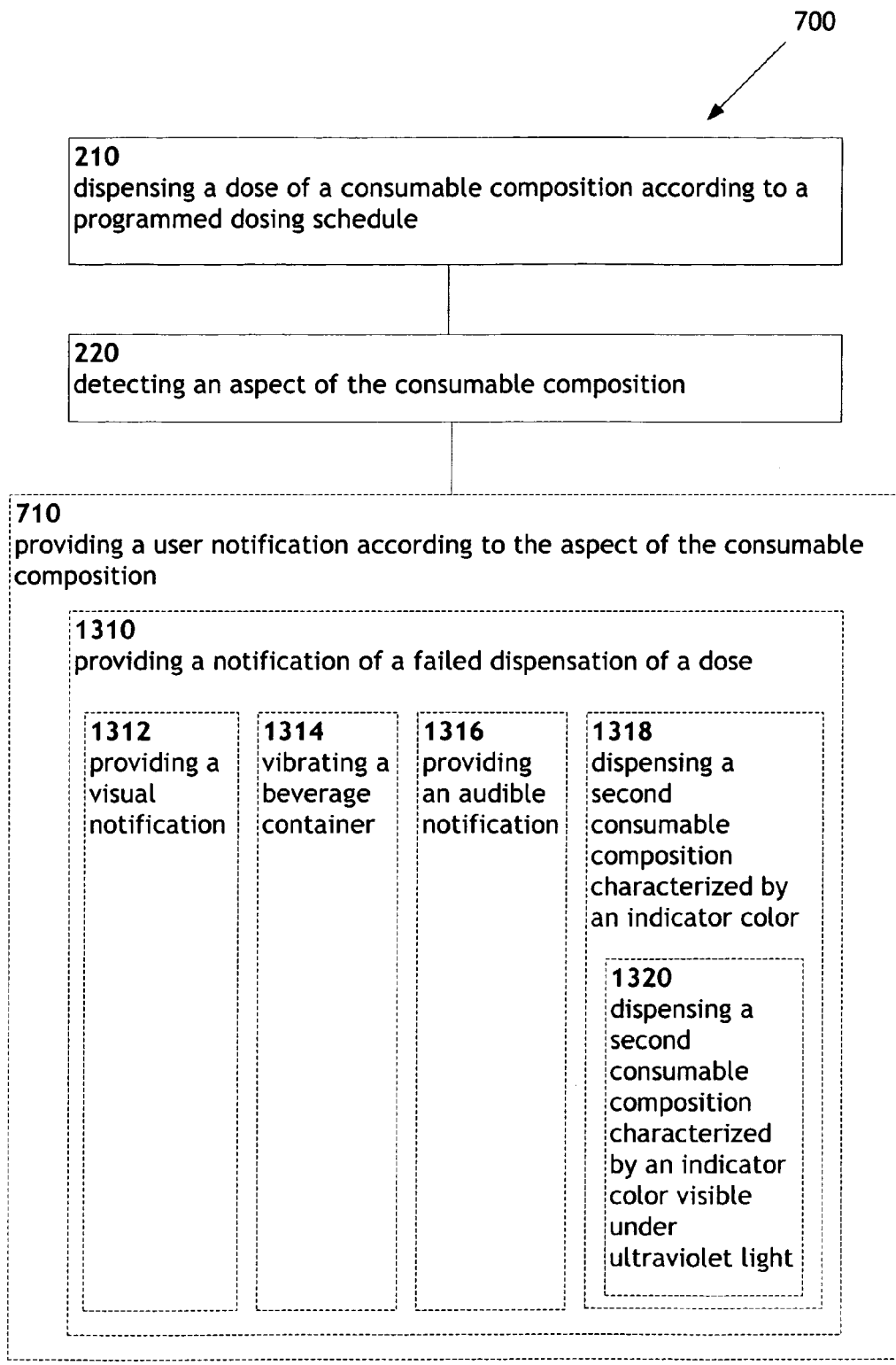
FIG. 13 is a high-level logic flowchart of a process depicting alternate implementations of FIG. 7.

FIG. 13 illustrates alternative embodiments of example operational flow 700 of FIG. 7. FIG. 13 illustrates an example embodiment where the user notification operation 710 may include at least one additional operation. Additional operations may include an operation 1310.

At operation 1310, providing a notification of a failed dispensation of a dose may occur (e.g. a dose scheduled to have been dispensed according to a programmed dosing schedule has not been dispensed). For example, as shown in FIG. 1, the user interface logic 123 may cause the notification module 142 of the user interface 140 to provide a notification that an amount of the consumable composition has failed to dispense (e.g., an audio notice stating "A dispensation of your Vicodin has failed.") The notification may include the identity of the consumable composition and the timing of the dispensation.

FIG. 13 further illustrates alternative embodiments of the example operational flow 700 of FIG. 7. FIG. 13 illustrates example embodiments where the failed dispensation of a dose notification operation 1310 may include at least one additional operation. Additional operations may include an operation 1312, an operation 1314, an operation 1316, an operation 1318, and/or an operation 1320.

At the operation 1312, providing a visual notification may occur (e.g. a textual display on an LCD display). For example, as shown in FIG. 1, the notification module 142 of the user interface 140 may include a flashing LED, LCD display screen, and the like.

At the operation 1314, vibrating a beverage container may occur (e.g. a spring-loaded mass may be released). For example, as shown in FIG. 1, the beverage container 110 may include an asymmetrical rotating mass operably coupled to a motor. Upon application of power to the motor, the mass may be rotated such that it induces vibration in the beverage container 110.

At the operation 1316, providing an audible notification may occur (e.g. the mechanical ringing of a bell). For example, as shown in FIG. 1, the notification module 142 of the user interface 140 may include a speaker assembly, and the like.

At the operation 1318, dispensing a second consumable composition characterized by an indicator color may occur. For example, as shown in FIG. 1, the dispensing logic 125 may cause the integrated consumable composition dispenser module 160 and/or the external consumable composition dispenser module 170 to dispense a second consumable composition (e.g., Brilliant Blue FCF) separate from the consumable composition (e.g., riboflavin) which has a visible indicator color (e.g., blue) distinct from that of the consumable composition (e.g. yellow). Further, at the operation 1320, dispensing a second consumable composition characterized by an indicator color visible under ultraviolet light may occur (e.g., chlorophyll extract).

Figure 14:
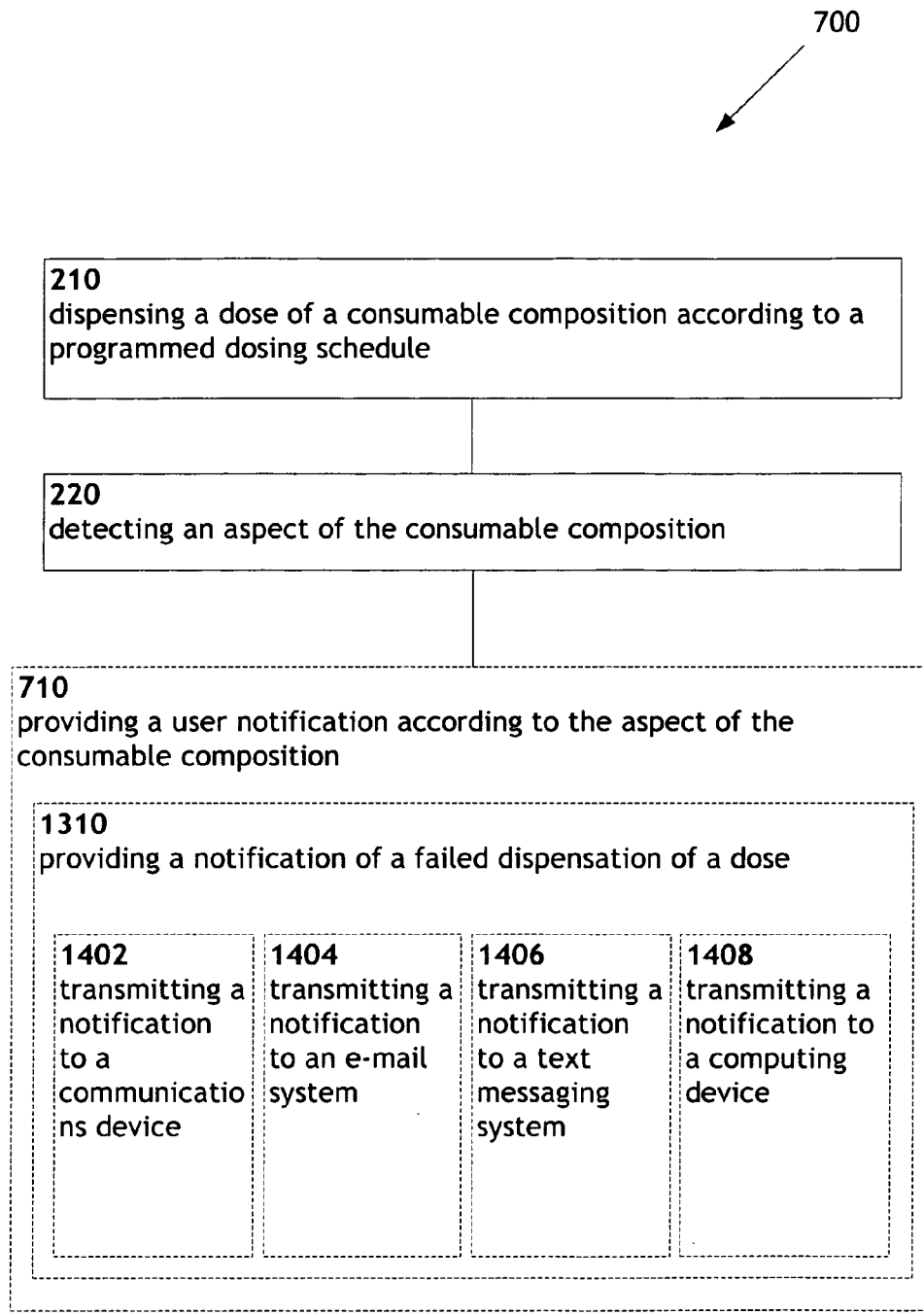
FIG. 14 is a high-level logic flowchart of a process depicting alternate implementations of FIG. 7.

FIG. 14 illustrates alternative embodiments of the example operational flow 700 of FIG. 7. FIG. 14 illustrates example embodiments where the failed dispensation of a dose notification operation 1310 may include at least one additional operation. Additional operations may include an operation 1402, an operation 1404, an operation 1406, and/or an operation 1408.

At the operation 1402, transmitting a notification to a communications device may occur (e.g., an automated voicemail sent to a cell phone and/or land line phone). For example, as shown in FIG. 1, the communications module 130 may transmit a notification to a monitoring system 180 linked to a communications device 181. The communications device 181 may include a cell phone, Blackberry®, land-line phone, and the like.

At the operation 1404, transmitting a notification to an e-mail system may occur (e.g. an e-mail to an IMAP, POP3, SMTP, and/or HTTP e-mail server having an e-mail account associated with a user 190). For example, as shown in FIG. 1, the communications module 130 may transmit a notification to a monitoring system 180 linked to an e-mail system 182.

At the operation 1406, transmitting a notification to a text messaging system may occur (e.g. text message to an SMS system in GSM). For example, as shown in FIG. 1, the communications module 130 may transmit a notification to a monitoring system 180 linked to a text messaging system 183.

At the operation 1408, transmitting a notification to a computing device may occur (e.g., an instant message to a music player via a music download service, such as the iTunes® service marketed by Apple® Inc.). For example, as shown in FIG. 1, the communications module 130 may transmit a notification to a monitoring system 180 linked to a computing device 184. The computing device 184 may include a personal digital assistant (PDA), personal computer, laptop, music player, gaming device, and the like.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A method for administering a consumable composition, the method comprising:
   obtaining dosing schedule data associated with a consumable composition regimen;
   dispensing at least one dose of a consumable composition into a container according to the dosing schedule data associated with a consumable composition regimen; and
   detecting at least one indication of at least one ingestion of the consumable composition via from data from at least one sensor configured to measure at least one property selected from: a physical property, a chemical property, an optical property or an electrical property.

2. A system for administering a consumable composition, the system comprising:
   a computing device configured for obtaining dosing schedule data associated with a consumable composition regimen;
   a dispenser module configured for dispensing at least one dose of a consumable composition into a container according to the dosing schedule data associated with a consumable composition regimen; and
   at least one sensor configured for detecting at least one indication of at least one ingestion of the consumable composition via measurement of at least one of: a physical property, a chemical property, an optical property or an electrical property.

3. The system of claim 2, wherein the at least one sensor configured for detecting at least one indication of at least one ingestion of the consumable composition includes:
   at least one sensor configured for detecting a presence of a bodily fluid.

4. The system of claim 2, wherein the dispenser module configured for dispensing of at least one dose of a consumable composition into a container according to the dosing schedule data associated with a consumable composition regimen includes:
   a dispenser module configured for delaying dispensing a second dose of the consumable composition until a detection of the at least one ingestion of the consumable composition.

5. The system of claim 2, wherein the at least one sensor configured for detecting at least one indication of at least one ingestion of the consumable composition includes:
   at least one sensor configured for detecting a movement of the container containing the consumable composition.

6. The system of claim 2, wherein the at least one sensor configured for detecting at least one indication of at least one ingestion of the consumable composition includes:
   at least one sensor configured for detecting a pressure applied to the container containing the consumable composition.

7. The system of claim 2, wherein the at least one sensor configured for detecting at least one indication of at least one ingestion of the consumable composition includes:
   at least one sensor configured for detecting a volume of fluid in of the container containing the consumable composition.

8. The system of claim 2, wherein the at least one sensor configured for detecting at least one indication of at least one ingestion of the consumable composition includes:
   at least one sensor configured for detecting a mass of fluid in of the container containing the consumable composition.

9. The system of claim 2, wherein the at least one sensor configured for detecting at least one indication of at least one ingestion of the consumable composition includes:
   at least one sensor configured for detecting a capacitance of fluid in of the container containing the consumable composition.

10. The system of claim 2, wherein the at least one sensor configured for detecting at least one indication of at least one ingestion of the consumable composition includes:
    at least one sensor configured for detecting an outflow rate of the consumable composition from of the container containing the consumable composition.

11. The system of claim 10, wherein the at least one sensor configured for detecting an outflow rate of the consumable composition from of the container containing the consumable composition includes:
    at least one sensor configured for detecting a rate of change of a volume of a fluid in of the container containing the consumable composition.

12. The system of claim 10, wherein the at least one sensor configured for detecting an outflow rate of the consumable composition from of the container containing the consumable composition includes:
    at least one sensor configured for detecting a rate of change of a mass of a fluid in of the container containing the consumable composition.

13. The system of claim 10, wherein the at least one sensor configured for detecting an outflow rate of the consumable composition from of the container containing the consumable composition includes:
    at least one sensor configured for detecting a rate of change of a capacitance of a fluid in of the container containing the consumable composition.

14. The system of claim 2, wherein the at least one sensor configured for detecting at least one indication of at least one ingestion of the consumable composition includes:
    at least one sensor configured for detecting a degree of inclination of the container containing the consumable composition.

15. A non-transitory computer readable medium including one or more computer readable instructions for execution of a process on a computing device, the process comprising:
    obtaining dosing schedule data associated with a consumable composition regimen;
    dispensing at least one dose of a consumable composition into a container according to the dosing schedule data associated with a consumable composition regimen; and
    detecting at least one indication of at least one ingestion of the consumable composition from data received from at least one sensor, the data including at least one of: physical property data, chemical property data, optical property data or electrical property data.

* * * * *

UNITED STATES PATENT AND TRADEMARK OFFICE
CERTIFICATE OF CORRECTION

| | | |
|---|---|---|
| PATENT NO. | : 8,718,817 B2 | Page 1 of 2 |
| APPLICATION NO. | : 12/001061 | |
| DATED | : May 6, 2014 | |
| INVENTOR(S) | : Hyde et al. | |

It is certified that error appears in the above-identified patent and that said Letters Patent is hereby corrected as shown below:

In the claims

In column 16, line 2, claim 7 "fluid in of the container containing the consumable composition" replace with the following --fluid in the container containing the consumable composition--

In column 16, lines 7-8, claim 8 "fluid in of the container containing the consumable composition" replace with the following --fluid in the container containing the consumable composition--

In column 16, line 14, claim 9 "fluid in of the container containing the consumable composition" replace with the following --fluid in the container containing the consumable composition--

In column 16, line 20, claim 10 "of the consumable composition from of the container" replace with the following --of the consumable composition from the container--

In column 16, line 24, claim 11 "composition from of the container containing the consumable" replace with the following --composition from the container containing the consumable--

In column 16, line 27, claim 11 "of a volume of a fluid in of the container containing the" replace with the following --of a volume of a fluid in the container containing the--

In column 16, line 31, claim 12 "composition from of the container containing the consumable" replace with the following --composition from the container containing the consumable--

In column 16, lines 34-35, claim 12 "of a mass of a fluid in of the container containing the consumable" replace with the following --of a mass of a fluid in the container containing the consumable--

In column 16, line 38, claim 13 "composition from of the container containing the consumable" replace with the following --composition from the container containing the consumable--

Signed and Sealed this
Twenty-second Day of July, 2014

Michelle K. Lee
*Deputy Director of the United States Patent and Trademark Office*

In column 16, line 41, claim 13 "of a capacitance of a fluid in of the container containing" replace with the following --of a capacitance of a fluid in the container containing--